Figure 1:
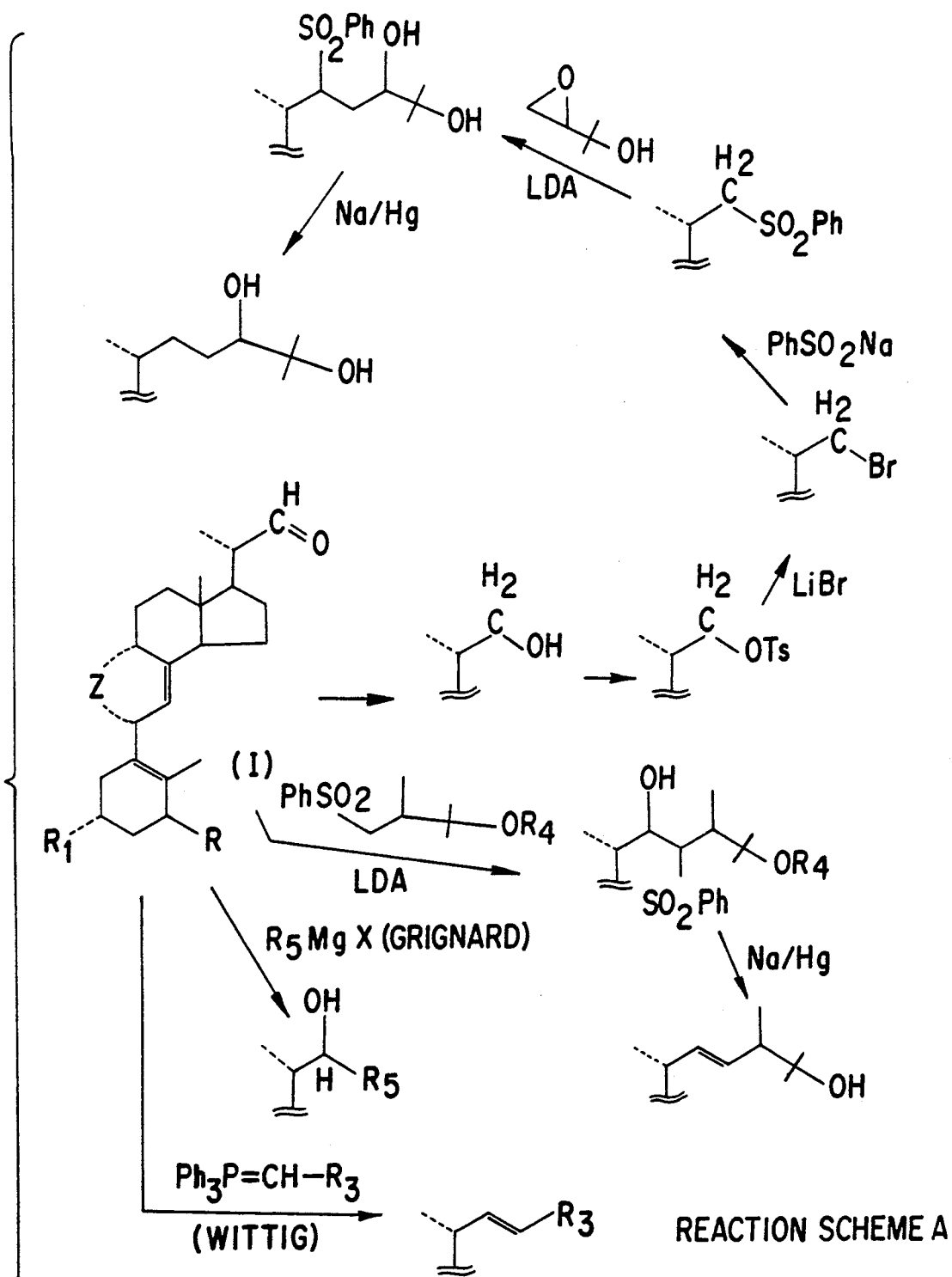
Figure 2:
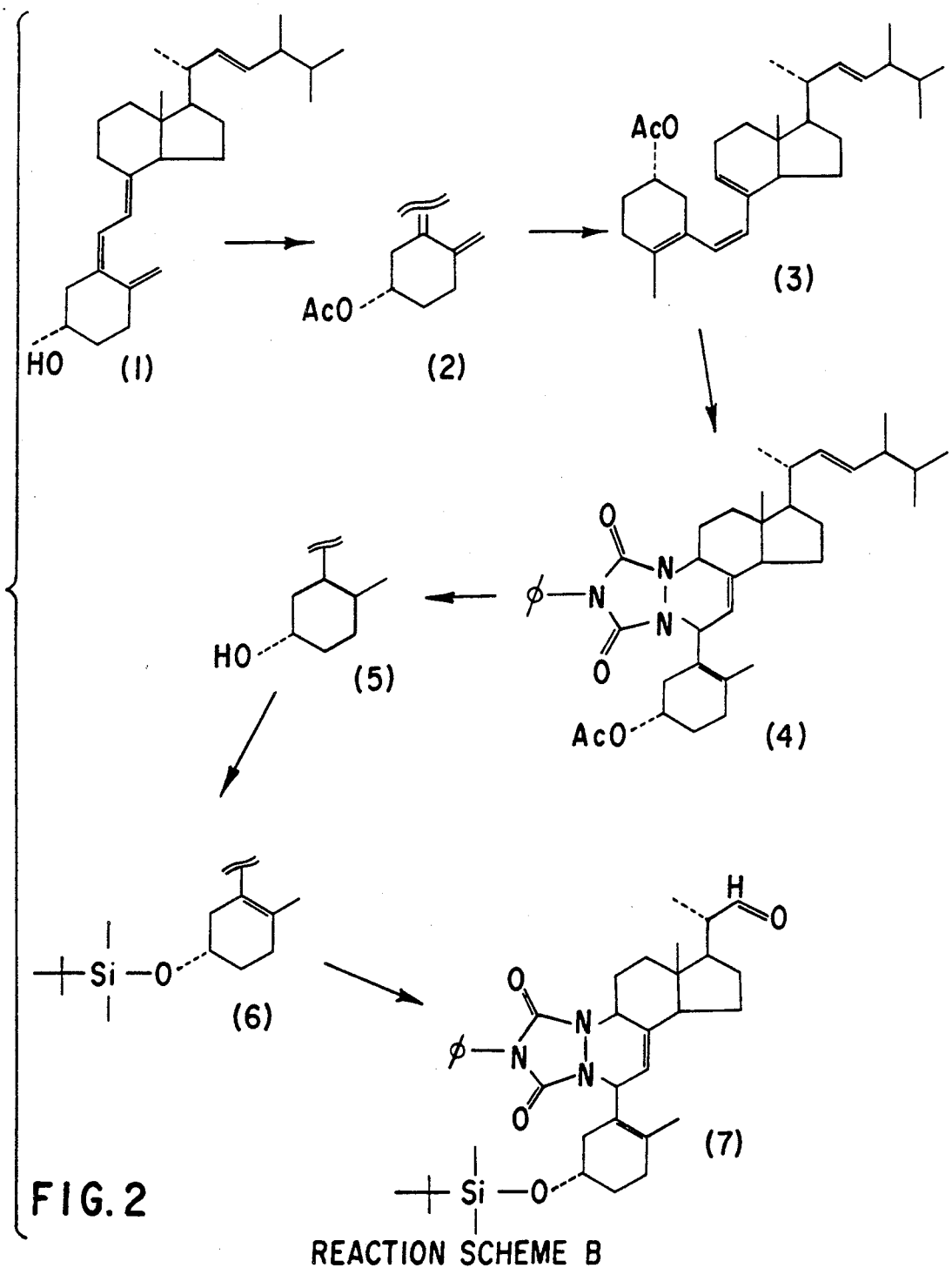
Figure 3:
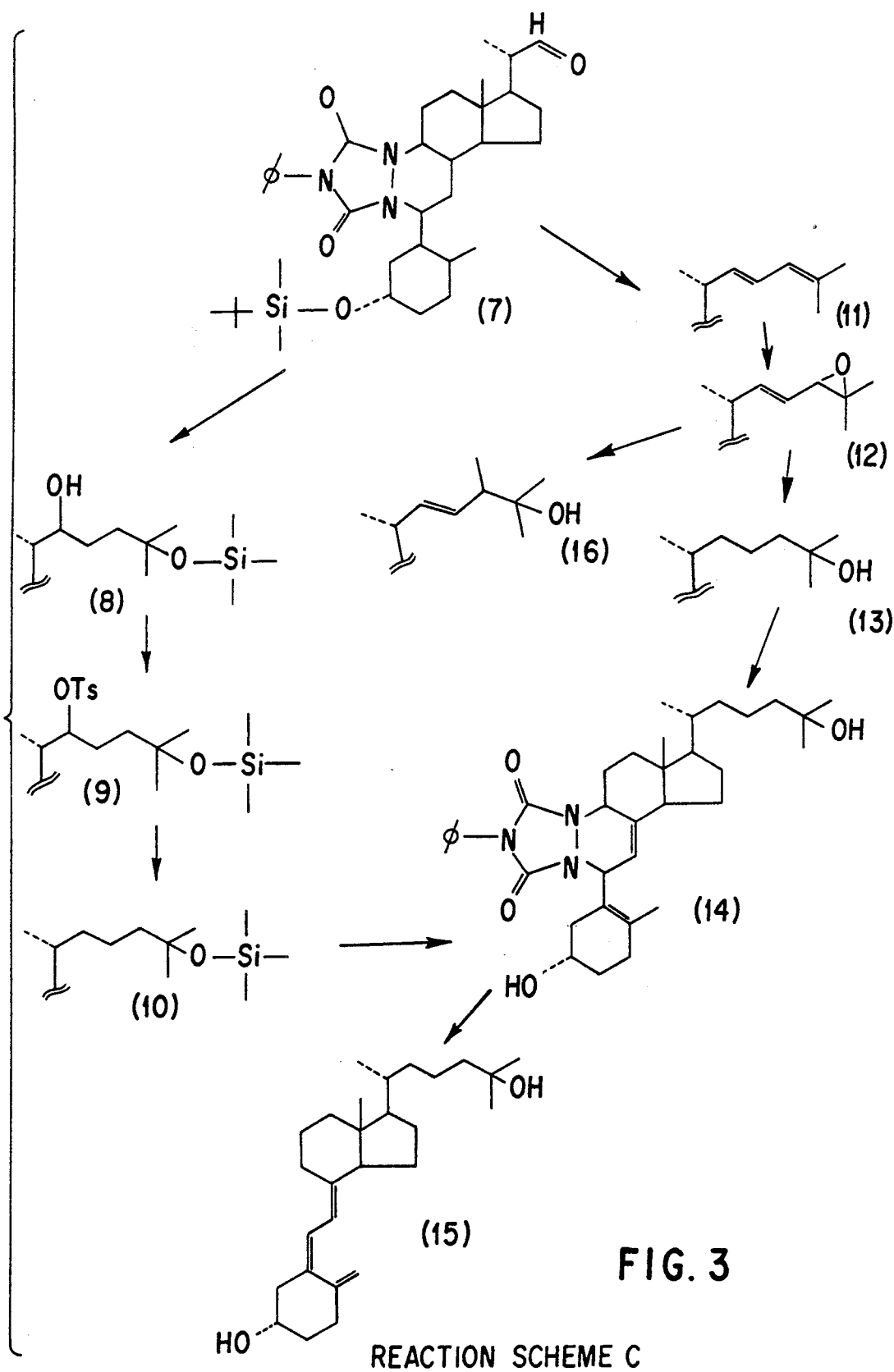

United States Patent [19]
Halkes et al.

[11] Patent Number: 5,110,924
[45] Date of Patent: May 5, 1992

[54] ADDUCT-ALDEHYDE AND ITS USE FOR THE PREPARATION OF VITAMIN-D COMPOUNDS

[75] Inventors: Sebastianus J. Halkes; Wilhelmus R. M. Overbeek, both of Weesp, Netherlands

[73] Assignee: Duphar International Research B.V., Weesp, Netherlands

[21] Appl. No.: 536,761

[22] Filed: Jun. 12, 1990

[30] Foreign Application Priority Data

Jun. 15, 1989 [NL] Netherlands ............ 8901513

[51] Int. Cl.[5] ............ C07D 237/26; C07D 487/04; C07D 333/50
[52] U.S. Cl. .................. 544/233; 544/234; 549/40; 552/653
[58] Field of Search ........... 544/233, 234; 549/40

[56] References Cited

U.S. PATENT DOCUMENTS 4,539,153 9/1985 Vandewalle et al. .......... 544/233
4,772,433 9/1988 Hesse ............ 544/233

OTHER PUBLICATIONS

Andrews et al., *J. Org. Chem.*, 51, p. 4819 (1986).
"Organic Chemistry", by Hendrickson, Cram, Hammond (3rd Ed.) pp. 508–509 (1970).
Salmond et al., J. Org. Chem., vol. 43, No. 4, 1978, pp. 790–791, *A Stereoselective Witting Reagent and its Application* . . . .
Kutner et al., Tetrahedron Letters, vol. 28, No. 49, pp. 6129–6132, 1987, *Vitamin D C-22 Aldeydes.*

Primary Examiner—Mukund J. Shah
Assistant Examiner—E. Bernhardt
Attorney, Agent, or Firm—Stevens, Davis, Miller & Mosher

[57] ABSTRACT

The invention relates to an adduct-aldehyde of the general formula

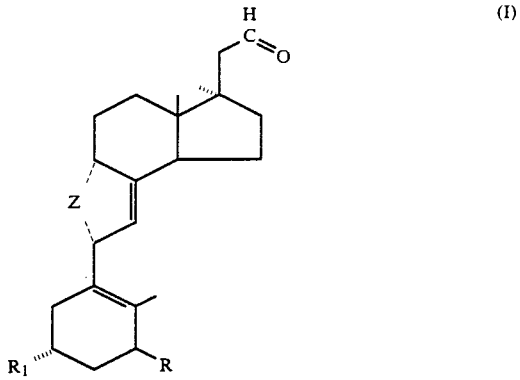

wherein
R is a hydrogen atom or an optionally etherified or esterified hydroxy group,
$R_1$ is an optionally etherified or esterified hydroxy group, and
Z is a sulphonyl group or a group of the general formula

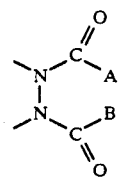

wherein A and B are equal or different and represent $C_1$–$C_4$ alkoxy groups, or wherein A and B together constitute a phenylimino group or a o-phenylene group.

The invention also relates to a method of preparing said adduct-aldehyde and to the use of said aldehyde as an intermediate for the preparation of vitamin-D compounds.

1 Claim, 3 Drawing Sheets

REACTION SCHEME A

LDA = LITHIUM DIISOPROPYL AMINE
R4 = HYDROXY PROTECTING GROUP
R5 = HYDROCARBYL
X = HALOGEN

REACTION SCHEME B

REACTION SCHEME C

ADDUCT-ALDEHYDE AND ITS USE FOR THE PREPARATION OF VITAMIN-D COMPOUNDS

The invention relates to an adduct-aldehyde, to a method of preparing the same, and to the use of said aldehyde as an intermediate for the preparation of vitamin-D compounds.

It is generally known that vitamin-D compounds have a strong biological activity and may be used in all those cases in which problems with the calcium metabolism play a part. A few years ago it was found that various active vitamin-D compound still have other pharmacotherapeutic activities and may be used successfully, for example, for the treatment of certain skin and bone diseases and for diseases which are related to cell differentiation. It is therefore of the utmost, importance to have the disposal of an arsenal of active vitamin-D compounds for said various application fields so as to be able to make the best possible choice of vitamin-D compound for the application in view.

Vitamin-D compounds which are of interest for the applications mentioned hereinbefore are hydroxylated vitamin-D compounds, for example, $1\alpha$-hydroxyvitamin-$D_3$ or $1\alpha$-hydroxycholecalciferol, 24R-hydroxyvitamin-$D_3$, $1\alpha,25$-dihydroxyvitamin-$D_3$, 25-hydroxyvitamin-$D_3$, 24R,25-dihydroxyvitamin-$D_3$, $1\alpha,24R$-dihydroxyvitamin-$D_3$, $1\alpha,24R,25$trihydroxyvitamin-$D_3$, $1\alpha,25$-dihydroxyvitamin-$D_3$-26,23-lactone, 25-hydroxyvitamin-$D_3$-26,23-lactone, 22-oxo-$1\alpha$-hydroxyvitamin-$D_3$, 22-oxo-$1\alpha,25$-dihydroxyvitamin-$D_3$, 24-oxo-$1\alpha$-hydroxyvitamin-$D_3$, 24-oxo-$1\alpha,25$-dihydroxyvitamin-$D_3$, vitamin-$D_2$ compounds hydroxylated in the $1\alpha$-,24- and/or 25-position(s), 22-oxa-substituted vitamin $D_3$ derivatives, and vitamin-D compounds having elongated $C_{17}$-side chains, such as 24,24-dihomo compounds and 24,24,24-trihomo compounds with or without double bonds and/or hydroxy groups in said chains, as well as related vitamin-D compounds having a $C_3$-$C_6$ cycloalkyl group, e.g. a $C_{24}$-cyclopropyl group, in the $C_{17}$-side chain; an example of this latter type of compounds is (1S,1'E,3R,5Z,7E,20R)-9,10-seco-20-(3'-cyclopropyl-3'-hydroxyprop-1'-enyl)-1,3-dihydroxypregna-5,7,10(19)-triene. Furthermore, fluorinated, optionally hydroxylated vitamin-D compounds are of importance due to their biological activities.

A convenient manner of introducing a hydroxy group in the $1\alpha$-position of a vitamin-D compound is described in European Patent Specification 70588 in the name of the Applicants. However, a solution which is satisfactory in every respect has not yet been found for modifying the $C_{17}$-side chain of vitamin-D compounds. As a matter of fact, both the starting materials for the preparation of such side chain-modified vitamin-D compounds must be easily available or accessible, and the multistep preparation process must lead to the intended purpose with sufficient selectivity and efficiency. In addition, said purpose is not a specifically defined substance, but a variety of $C_{17}$-side chain-modified vitamin-D compounds, as indicated hereinbefore, from which a selection may be made at will. This means that the preparation process should be suitable without fundamental changes for the synthesis of an as large as possible number of different vitamin-D compounds.

The methods for the synthesis of active vitamin-D compounds, in particular active vitamin-D metabolites, described in literature, are unsatisfactory with regards to one or several of the above requirements. In order to meet the last-mentioned requirement, various investigators have suggested to use in the synthesis of side-chain-modified vitamin-D compounds an aldehyde as a "versatile intermediate" and to use the reactivity of the aldehyde function for building up the desired $C_{17}$-side chain. Both Salmond and coworkers (J. Org. Chem. 43, 1978, 790–793) and Kutner and coworkers (Tetrahedron Letters 28, 1987, 6129–6132), however, use starting materials which are difficult of access or are not readily available, while in addition the aldehydes to be used as "key intermediates" cannot be converted with satisfactory yields into the desired vitamin-D compounds, in particular 25-hydroxyvitamin-D metabolites. Andrews and coworkers (J. Org. Chem. 51, 1986, 4819–4828) use as a "key intermediate" in the synthesis of 25-hydroxyvitamin-D metabolites a vitamin D $C_{22}$-aldehyde, in which the sensitive triene system of vitamin-D is protected by a Diels-Alder reaction with 4-phenyl-1,2,4-triazolin-3,5-dione or with phtalazine-1,4-dione, the dienophile being attached to the sites 6 and 19 of the vitamin-D molecule. However, in this method an additional photoisomerisation is ultimately necessary to regenerate the vitamin-D system, which involves losses of expensive final product and contamination of said final product.

It is the object of the invention to provide an aldehyde which may be used as an intermediate for the preparation of a vitamin-D compound and which does not exhibit the disadvantages mentioned hereinbefore.

According to the present invention this object can be achieved with a $C_{22}$-aldehyde which is derived from a previtamin-D derivative and has the following general formula:

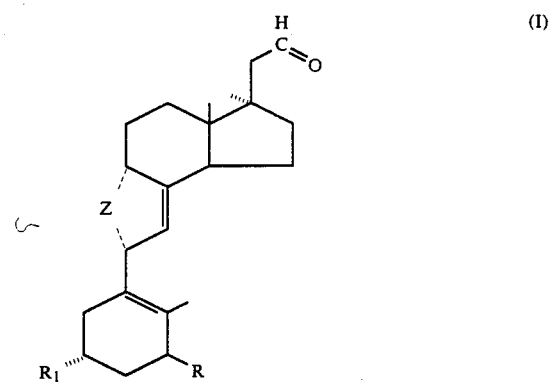

wherein
R is a hydrogen atom or an optionally etherified or esterified hydroxy group,
$R_1$ is an optionally etherified or esterified hydroxy group, and
Z is a sulphonyl group or a group of the general formula

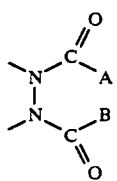

wherein A and B are equal or different and represent $C_1$-$C_4$ alkoxy groups, or wherein A and B together constitute a phenylimino group or an o-phenylene group.

Previtamin-D compounds are known in literature. Velluz and coworkers (Bull. Soc. Ch. Fr. 1949, 501) discovered previtamin-D$_3$ already in 1949, while Koevoet et al (Recueil 74, 1955, 788–792) devoted an article to this compound in 1955. It appears from these publications that previtamin-D$_3$ can be obtained by equilibration from vitamin-D$_3$ can be obtained by equilibration from vitamin-D$_3$ but can change again into the starting substance very easily. Moreover, previtamin-D$_3$ is not crystalline and can hence almost not be obtained in a pure form. This instability and difficulty of manipulation will most probably have been the cause that so far little attention has been paid in literature to previtamin-D compounds for synthetic purposes. In fact, the same applies to a stereoisomer of previtamin-D$_3$, viz. tachysterol, which is also discussed by Koevoet et al in Recueil 74, 1955, 788–792.

A previtamin-D$_2$ compound may be used as a starting substance for the above aldehyde, which compound can be obtained from a vitamin-D$_2$ compound in the same manner as previtamin-D$_3$, namely by equilibration. This equilibration reaction is temperature-dependent; the formation of a previtamin-D$_2$ compound can be stimulated by raising the temperature. A tachysterol$_2$ compound may also be used as a starting substance. Alternatively, irradiation of an ergosterol compound at low temperature also yields the desired previtamin-D$_2$ compound. After the hydroxy group or groups present in the molecule optionally has/have been protected, an addition may be carried out with a suitable dienophile as described in the European Patent Specification 70588 mentioned hereinbefore. Then a previtamin-D$_2$ adduct is formed of the general formula

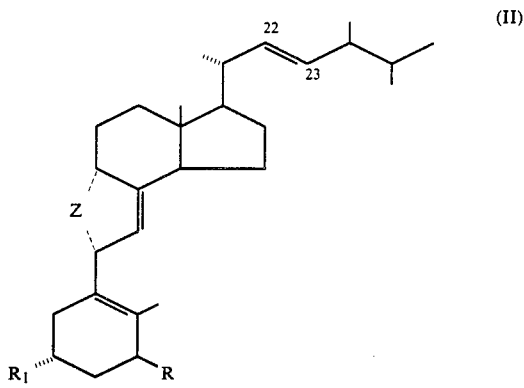

(II)

Suitable dienophiles for the above addition reaction are SO$_2$ and compounds of the general formula

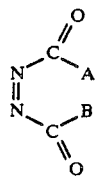

wherein A and B have the meanings as mentioned hereinbefore. As examples of suitable dienophiles which satisfy the last-mentioned formula may be mentioned 1,2,4-triazoline-3,5-diones which are substituted in the 4-position by an optionally substituted phenyl group, 1,4-phthalazine-dione and de(C$_1$-C$_4$)alkylazodicarboxylates. Due to the simple adduct formation and the easy removal afterwards 4-phenyl-1,3,4-triazoline-3,5-dione, dimethyl-azodicarboxylate, diethylazodicarboxylate or 1,4-phthalazine-dione is to be preferred as a dienophile. After the synthesis of the desired vitamin-D compound, the dienophile group Z can easily be removed from the adduct, in which, in contrast with the vitamin D adduct mentioned hereinbefore and synthesised by Andrews and coworkers, the steric configuration is maintained and the desired cis-vitamin-D compound is formed directly.

Hydroxy groups in the adduct interfering with the reaction may be protected before or after the adduct formation by a reaction with an esterification or etherification agent. A suitable esterification agent is an alkylchlorocarbonate having 2 to 5 carbon atoms, or an aromatic carboxylic acid, a saturated aliphatic carboxylic acid having 1 to 4 carbon atoms, p-toluenesulphonic acid, methanesulphonic acid, trifluoroacetic acid or a derivative of these acids suitable for the esterification reaction. In order to protect unstable hydroxy groups in the form of an ether, in principle any etherification agent known for this purpose is suitable: for example, a triphenylmethylhalide, 2,3-dihydropyrane, or a trialkylsilylhalide or trialkylsilylethoxymethylhalide the alkyl groups of which have 1 to 6 carbon atoms. Particularly suitable for this purpose are trimethylsilylchloride, tert.-butyldimethylsilylchloride or trimethylsilyl-ethoxymethylchloride, because these etherification agents readily react with the hydroxy group to be protected to form an ether function, which on the one hand is sufficiently stable under the reaction conditions used but on the other hand can easily be removed to recover the original hydroxy group; tert.-butyl dimethylsilylchloride is to be preferred, because the tert.-butyl dimethylsilyl group has been found to be exellently suitable as a protective group.

Previtamin-D$_2$ adducts which are excellently accessible by the addition of dienophiles to readily available raw materials are adducts of the general formula II, wherein R is a hydrogen atom. These adducts can easily be converted to the corresponding compounds hydroxylated in the 1-position, preferably the 1α-position, by means of the process described in the European Patent Specification 70588 mentioned hereinbefore. In this manner previtamin-D$_2$ adducts are formed of the general formula II, wherein R is a hydroxy group or an optionally protected hydroxy group. Of course it is not necessary to introduce the 1-hydroxy group in this stage of the synthesis of the desired vitamin-D compound. The hydroxylation reaction described in the European Patent Specification 70588 for the preparation of 1-hydroxy substituted vitamin D compounds may also be carried out in a later stage of the synthesis, namely when, by building up the C$_{17}$ side chain, the desired vitamin-D compound is synthesised but before the dienophile group A is removed.

It has been found that the C$_{22}$-aldehyde of the general formula I can be prepared in a simple manner by subjecting the above previtamin-D$_2$ adduct of the general formula II to an oxidation which is selective for the C$_{22}$–C$_{23}$ double bond. Such a conversion can be effected with an excellent yield by first reacting the previtamin-D$_2$ adduct with ozone, preferably in the presence of an organic base (e.g. pyridine), and by then reducing the formed ozonide. It has been found surprisingly that in this conversion the steric configuration at $C_{20}$ is maintained, although in comparable conversion, for example, as described by Salmond and Sobala (Tetrahedron Letters 20, 1977, 1695–1698), epimerisation at $C_{20}$ easily occurs.

The resulting $C_{22}$-aldehyde of the general formula I is a very suitable intermediate for the preparation of a large number of different vitamin-D compounds with varying $C_{17}$-side chains. More in particular, the $C_{22}$-aldehyde may be used for the preparation of a vitamin-D compound of the general formula

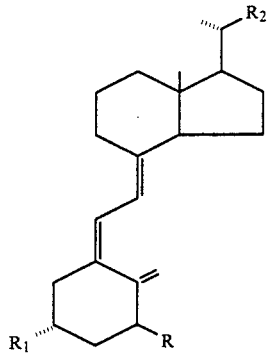

wherein
R and $R_1$ have the meanings given hereinbefore, and
$R_2$ is a branched or non-branched, saturated or unsaturated aliphatic hydrocarbyl or hydrocarbyloxy radical which comprises 1 to 14 carbon atoms and is optionally substituted with one or more groups, selected from hydroxy groups, ether groups, oxo functions, cycloalkyl groups having 3–6 carbon atoms, lactone groups and/or fluorine atoms,
by subjecting the aldehyde of the general formula I to a chain-extending reaction, generally in a series of successive reaction steps, in which the aldehyde function is converted into the group $R_2$, and by then removing the group Z in a manner known per se.

The removal of the dienophile group Z may be carried out in a simple manner, for example, by means of a base in a protic or aprotic polar solvent or a mixture thereof, as described in the European Patent Specification 70588 mentioned hereinbefore. Suitable systems for this purpose are an alkali metal hydroxide in an alcohol, for example, methanol or n-butanol, a metal hydride, for example, lithium aluminium hydride, in an inert aprotic solvent, or an alkali metal alkoxide in an alcohol. The removal of the groups which protect the hydroxy function(s) may also take place in a manner which is known per se for the removal of such groups. For example, protective silylether groups can be removed with a fluorine compound, for example, tetrabutyl ammonium fluoride, in an inert organic solvent, for example, an ether such as tetrahydrofuran. Removal with an acid, optionally adsorbed to a carrier, e.g. silicon dioxide, is also possible.

It has been found that the $C_{22}$-aldehyde of the general formula I shown hereinbefore is excellently suitable for a chain-extending reaction. In this reaction the desired side chain is built up at $C_{17}$, usually in a number of successive synthetic steps. In this manner the aldehyde function of the $C_{22}$-aldehyde in question may be converted into the group $R_2$ (formula III) via a Grignard reaction or via a Wittig reaction (see scheme A attached). It has been found that Grignard reagents and Wittig reagents are particularly suitable to enter into reaction with the $C_{22}$-aldehyde of the general formula I. In this manner the carbon skeleton of the desired $C_{17}$ side chain can simply be realised. Modifications of the said side chain, for example, the introduction of hydroxy groups, oxo functions, fluorine atoms and the like, can be realised, if desired, in a subsequent reaction. Particularly suitable for a reaction with the $C_{22}$-aldehyde of the general formula I is a Wittig reagent of the general formula $$Ph_3P\!=\!CH\!-\!R_3,$$

wherein
Ph is a phenyl group, and
$R_3$ is a hydrogen atom or a branched or non-branched, saturated or unsaturated aliphatic hydrocarbyl radical which is optionally substituted with one or more etherified or esterified hydroxy groups or fluorine atoms and which comprises 1 to 13 carbon atoms,
because such a reagent easily reacts with the aldehyde and leaves the other functions in the aldehyde intact.

Another particularly suitable chain-extending reaction is the conversion of the $C_{22}$-aldehyde to a sulphone intermediate, preferably a 22-arylsulphonyl-24-hydroxy-substituted compound or a 23-arylsulphonyl-22-hydroxy-substituted compound, in a manner known per se for related compounds, followed by a desulfonylation reaction. Examples of such chain-extending reactions are shown in reaction scheme A attached.

The invention finally relates to a method of preparing a vitamin-D compound of the general formula III shown above, in which the $C_{22}$-aldehyde of the general formula I is used as an intermediate. In performing this method, (a) previtamin-$D_2$ adduct of the general formula II shown above is subjected to an oxidation which is selective for the $C_{22}$–$C_{23}$ double bond, preferably by reacting the previtamin-$D_2$ adduct with ozone and by then reducing the formed ozonide, and thereupon (b) the aldehyde of the general formula I thus obtained is subjected to a chain-extending reaction in which the desired $C_{17}$-side chain is formed, after which is dienophile group Z is removed in a manner known per se.

The invention will now be described in greater detail with reference to the ensuing specific examples. The reactions are recorded in the attached reaction schemes B and C, to which the numbers of the compounds refer.

EXAMPLE I

Preparation of the adduct of previtamin-$D_2$ acetate and 4-phenyl-1,2,4-thiazoline-3,5-dione, and oxidation thereof to the desired $C_{22}$-aldehyde (a) A quantity of 40 ml of acetic acid anhydride is added to a solution of 22.5 g of vitamin-$D_2$ in 200 ml of dry pyridine. This reaction mixture is left to stand at room temperature for 16 hours. The solution is then poured on ice water and 1 liter of diethyl ether is added. After separation of the layers, the organic layer is washed three times with water and then successively with 2N hydrochloric acid, with a sodium bicarbonate solution and finally with a saturated NaCl-solution till neutral. After drying and evaporating under reduced pressure, a residue is obtained which is dissolved in little acetone. Cooling to $-20°$ C. provides the desired vitamin-$D_2$ acetate (2) in a yield of 22.3 g; melting point 88°.

(b) A quantity of 22.3 g of the resulting vitamin-$D_2$ acetate (2) is melted and kept at a temperature of approximately 100° C. for approximately 45 minutes. Approximately 30% is converted to previtamin-$D_2$ acetate (NMR analysis). After cooling 10.8 g of unconverted vitamin-$D_2$ acetate is recovered by crystallisation from acetone. The mother liquor weighs 11.4 g after evaporation, 6.7 g hereof being previtamin-$D_2$ acetate (3).

(c) A solution of 7.25 g of 4-phenyl-1,2,4-triazoline-3,5-dione in 90 ml of dry dichloromethane is added, under a nitrogen blanket and while stirring at 0° C., to a solution of previtamin-$D_2$ acetate (3), obtained according to (b), in 330 ml of dichloromethane; the calculated quantity of previtamin-$D_2$ acetate which is used is 18.14 g, i.e. equimolar with the starting quantity of triazolinedione.

After evaporation, the residue is recrystallised from ethanol and then yields the desired adduct (4) of previtamin-$D_2$ acetate and 4-phenyl-1,2,4-thiazoline-3,5-dione in a yield of 65%. Identification by means of NMR analysis; melting-point 126.3°–128° C.

(d) A solution of 13.33 g of the resulting pure adduct (4) in 200 ml of dry methanol in which 12 g of potassium carbonate have been suspended, is refluxed for 45 minutes. After evaporation under reduced pressure the residue is taken up in a mixture of water and diethyl ether. The organic layer is separated, washed successively with dilute acid, $Na_2CO_3$ solution and NaCl solution, and dried. After evaporating the solvent and recrystallising from acetone, the desired alcohol (5) is obtained in a yield of 12.04 g; characterisation by means of NMR and IR.

(e) A solution of 12.04 g of the resulting alcohol (5), 1.98 g of imidazole and 3.70 g of t.-butyl dimethylsilylchloride in 100 ml of dimethylformamide is stirred for 18 h under nitrogen at room temperature. Hexane is then added until complete dissolution, after which the dimethylformamide layer is separated from the hexane layer and extracted with hexane. The combined hexane fractions are washed successively with 0.1N hydrochloric acid, water, bicarbonate solution and NaCl solution and dried. After evaporation and recrystallisation from ethanol the desired t.-butyl dimethyl ether (6) is obtained in a yield of 83%, calculated on the starting acetate (4). Identification by means of NMR analysis; melting-point 147.4°–148.5° C.

The resulting adduct of previtamin-$D_2$ t.-butyl dimethyl silylether and 4-phenyl-1,2,4-triazoline-3,5-dione (6) may be hydroxylated selectively in the 1-position, optionally in the same manner as described in the European Patent Specification 70588 mentioned hereinbefore, the adduct of 1-hydroxyprevitamin-$D_2$-t.-butyl dimethyl silyl ether being formed.

(f) The resulting adduct of previtamin-$D_2$ t.-butyl dimethyl silyl ether and 4-phenyl-1,2,4-triazoline-3,5-dione is dissolved in a quantity of 40 g in 470 ml of methylene chloride to which 4.7 ml of dry pyridine has been added. At a temperature of −70° to −75° C. ozone is led through the solution at a rate of 0.6 mmol $O_3$/minute, the reaction being followed by means of thin-layer-chromatography (eluent-:toluene/acetone=95/5). Flushing with ozone is discontinued after 140 minutes and 23 g of zinc powder and 116 ml of glacial acetic acid are added at −70° to −75° C. The reaction mixture is slowly heated to room temperature while flushing with nitrogen, after which the mixture is refluxed for 8 minutes. After filtering off the excess of zinc, the filtrate is washed successively with NaCl solution, $Na_2CO_3$ solution. 2M sodium hydroxide solution and again NaCl solution. After drying and purifying over a silica gel column (elution with methylene chloride/acetone), the desired $C_{22}$-aldehyde adduct (7) is obtained in a yield of 28.04 g (78%). If desired, the product may be further purified by recrystallisation from acetone. Identification by means of NMR analysis; melting-point 195.7°–197.7° C.

EXAMPLE II

Modification of the $C_{22}$-aldehyde (7) by means of a Grignard reaction

So much dry diethyl ether is added to 2.6 g of magnesium that all the magnesium is covered by the ether. 1 g of the 10.5 g of 3-chloro-1,1-dimethylpropyl-trimethylsilylether necessary for the Grignard reagent is then added. The reaction is started by the addition of little dibromoethane, after which the reaction is maintained by the gradual addition of the silyl ether in a solution of 10 ml of dry diethyl ether at a temperature of approximately 38° C. After all the silyl ether has been added, the reaction mixture is refluxed for 30 minutes, while stirring.

Thereupon 10 g of the $C_{22}$-aldehyde (7) obtained according to example I in 20 ml of dry tetrahydrofuran is added dropwise, after which the reaction mixture is refluxed for 15 minutes while stirring. The reaction mixture is cooled to room temperature and 50 ml of saturated $NH_4Cl$ solution is then added. After washing with NaCl solution and drying, the reaction mixture is evaporated and separated on an adsorption column (eluent:toluene/acetone=95/5). The desired product (8) is obtained in a yield of 3.13 g. For the preparation of 25-hydroxyvitamin-$D_3$, product (8) is reacted with toluene sulphonyl chloride, the $C_{22}$-hydroxy group being converted into a tosyloxy group: (9). The trimethyl silyl ether of the desired $C_{17}$ side chain is formed by reduction with $LiAlH_4$ in dry diethyl ether: the adduct of 25-trimethyl silyloxy-previtamin-$D_3$-t.-butyl-dimethyl silyl ether and 4-phenyl-1,2,4-triazoline-3,5-dione (10). After the removing the protecting silyl ether groups and dienophile group, the desired 25-hydroxyvitamin-$D_3$ may be obtained herefrom. These cleavage reactions will be described in greater detail in Example IV.

EXAMPLE III

Modification of the $C_{22}$-aldehyde (7) by means of a Wittig reaction (a) The $C_{22}$-aldehyde (7) obtained according to example I is reacted in a quantity of 3.0 g with 2.9 g of the Wittig salt of triphenyl phosphine and 4-chloro-2-methyl-butene-2 in a solution of THF. The resulting product is recrystallised from diethyl ether and then provides the desired 22,24-diene-vitamin-$D_3$ adduct (11) in a yield of 79% (ratio 22-cis/22-trans=1:3). Identification by means of NMR.

(b) The resulting 22,24-diene-vitamin-$D_3$ adduct is epoxidised selectively on the $C_{24}$–$C_{25}$ double bond by means of a mixture of dibenzoyl peroxide and hexamethyl disilazane in a solution of methylene chloride. NMR analyses demonstrate that the 24,25-epoxide (12) consists of a stereoisomer mixture of 24,25-epoxides. The 22-ene-24-epoxy-vitamin-$D_3$ adduct (12) is purified by means of flash column chromatography (eluent:hexane/acetone=7/3); yield 60%.

(c) A solution of 1.0 g of the epoxy compound (12) in ethyl acetate is shaken at atmospheric pressure with 0.22 g of Raney nickel under a hydrogen atmosphere. The desired hydrogenation takes place according to NMR analysis. The 25-hydroxyvitamin-$D_3$ adduct (13) is formed in yield of 50%.

By a Grignard reaction of epoxy compound (12) with methyl magnesium chloride, after separation of the resulting isomer mixture the 25-hydroxyvitamin-$D_2$ adduct (16) is prepared, from which, by removing the protecting groups, as will be described in example IV, 25-hydroxyvitamin-$D_2$ is obtained.

EXAMPLE IV

Preparation of 25-hydroxyvitamin-$D_3$ by removing the protecting groups (a) The 25-hydroxyvitamin $D_3$ adduct (13) obtained according to example III is desilylated by dissolving 9.80 g in 90 ml of acetonitrile and adding to this solution 15 ml of an aqueous hydrofluoric acid solution (40–45%). The reaction mixture is stirred at room temperature in a nitrogen atmosphere for 3 hours. The ether cleavage is followed with thin-layer chromatography. After pouring the reaction mixture into 300 ml of water and adding 100 ml of methylene chloride, the organic layer is separated, washed successively with a 5% $NaHCO_3$ solution and a NaCl solution and dried. After evaporation of the solvent, the desired product (14) is purified by chromatography over a silica gel column (eluent:methylene chloride-acetone mixture); yield 86%. Identification by means of NMR.

In a corresponding manner the bis(silyl ether) obtained according to Example II is desilylated the addition product (14) also being formed.

(b) The resulting 25-hydroxyvitamin-$D_3$ adduct (14) is dissolved in a quantity of 500 mg in 25 ml of methanol. After the addition of 25 ml of 15N aqueous KOH-solution the reaction mixture is refluxed at 85° C. for 24 hours. The reaction mixture is then poured on a mixture of ice and water and extracted with diethyl ether. After washing successively with $NaHCO_3$ solution and NaCl solution, the organic phase is evaporated and provides the desired final product, namely 25-hydroxy-vitamin-$D_3$ (15) in a yield of 50%. The product can be recrystallised from acetone/water; melting point 108.4°–111.4° C.; identification by means of NMR analysis.

We claim:
1. An adduct-aldehyde of the formula

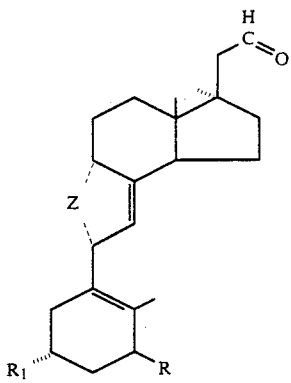

wherein
R is hydrogen or hydroxy which is optionally etherified by an etherification agent or esterified by an estherification agent,
$R_1$ is hydroxy which is optionally etherified by an etherification agent or esterified by an esterification agent, and
Z is sulphonyl or a group of the formula

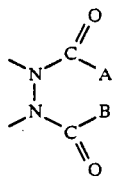

wherein A and B are equal or different and represent $C_1$–$C_4$ alkoxy, or wherein A and B together constitute phenylimino or o-phenylene,
the etherification agent being selected from the group consisting of triphenylmethylhalides, 2,3-dihydropyran, trialkylsilylhalides having 1 to 6 carbon atoms in the alkyl group and trialkylsilylethoxymethylhalides having 1 to 6 carbon atoms in the alkyl groups, and
the esterification agent being selected from the group consisting of alkylchlorocarbonates having 2 to 5 carbon atoms, saturated aliphatic carboxylic acids having 1 to 4 carbon atoms, p-toluenesulphonic acid, methanesulphonic acid, trifluoroacetic acid and derivatives of said acids suitable for the esterification reaction.

* * * * *